United States Patent
Flexman et al.

(10) Patent No.: US 11,844,576 B2
(45) Date of Patent: Dec. 19, 2023

(54) ENDOGRAFT VISUALIZATION WITH OPTICAL SHAPE SENSING

(71) Applicant: KONINKLIJKE PHILIPS N.V., Eindhoven (NL)

(72) Inventors: Molly Lara Flexman, Melrose, MA (US); Gregory Cole, Ossining, NY (US); David Paul Noonan, New York, NY (US); Neriman Nicoletta Kahya, Eindhoven (NL); Ehsan Dehghan Marvast, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 864 days.

(21) Appl. No.: 15/544,649

(22) PCT Filed: Jan. 8, 2016

(86) PCT No.: PCT/IB2016/050077
§ 371 (c)(1),
(2) Date: Jul. 19, 2017

(87) PCT Pub. No.: WO2016/116825
PCT Pub. Date: Jul. 28, 2016

(65) Prior Publication Data
US 2018/0008352 A1    Jan. 11, 2018

Related U.S. Application Data

(60) Provisional application No. 62/106,271, filed on Jan. 22, 2015.

(51) Int. Cl.
*A61B 34/20* (2016.01)
*A61B 34/10* (2016.01)
*A61B 17/00* (2006.01)
*A61F 2/07* (2013.01)
(Continued)

(52) U.S. Cl.
CPC .............. *A61B 34/20* (2016.02); *A61B 34/10* (2016.02); *A61B 2017/00778* (2013.01);
(Continued)

(58) Field of Classification Search
CPC .... A61B 2017/00778; A61B 2034/102; A61B 2034/2055; A61B 2034/2061;
(Continued)

(56) References Cited

U.S. PATENT DOCUMENTS 6,450,978 B1 * 9/2002 Brosseau ............... A61B 90/36
600/595
7,772,541 B2 * 8/2010 Froggatt .............. G01D 5/3539
250/227.23

(Continued)

FOREIGN PATENT DOCUMENTS

WO    2005/011499    9/2006
WO    2014/186715    11/2014

*Primary Examiner* — Christopher L Cook

(57) ABSTRACT

A system for medical device deployment includes an optical shape sensing (OSS) system (104) associated with a deployable medical device (102) or a deployment instrument (107). The OSS system is configured to measure shape, position or orientation of the deployable medical device and/or deployment instrument. A registration module (128) is configured to register OSS data with imaging data to permit placement of the deployable medical device. An image processing module (142) is configured to create a visual representation (102') of the deployable medical device and to jointly display the deployable medical device with the imaging data.

17 Claims, 8 Drawing Sheets

(51) Int. Cl.
   *A61F 2/91*      (2013.01)
   *A61F 2/954*     (2013.01)
   *A61F 2/958*     (2013.01)
   *A61F 2/95*      (2013.01)

(52) U.S. Cl.
   CPC . *A61B 2034/102* (2016.02); *A61B 2034/2055* (2016.02); *A61B 2034/2061* (2016.02); *A61F 2/07* (2013.01); *A61F 2/91* (2013.01); *A61F 2/954* (2013.01); *A61F 2/958* (2013.01); *A61F 2002/9534* (2013.01)

(58) Field of Classification Search
   CPC . A61B 34/10; A61B 34/20; A61F 2002/9534; A61F 2/07; A61F 2/91; A61F 2/954; A61F 2/958
   See application file for complete search history.

(56) References Cited

U.S. PATENT DOCUMENTS

| | | |
|---|---|---|
| 8,666,714 B2 | 3/2014 | Whirley et al. |
| 9,135,704 B2 | 9/2015 | Neuhauser et al. |
| 9,675,304 B2 | 6/2017 | Jain |
| 9,700,209 B2 | 7/2017 | Florent |
| 9,724,071 B2 | 8/2017 | Deladi |
| 2006/0106406 A1 | 5/2006 | Weinberger |
| 2006/0241469 A1* | 10/2006 | Rold .............. A61B 8/463 600/459 |
| 2008/0137923 A1 | 6/2008 | Spahn |
| 2009/0304245 A1 | 12/2009 | Egger et al. |
| 2012/0289777 A1 | 11/2012 | Chopra et al. |
| 2013/0035537 A1 | 2/2013 | Wallace et al. |
| 2013/0216025 A1 | 8/2013 | Chan |
| 2013/0303893 A1 | 11/2013 | Duindam et al. |
| 2013/0324833 A1 | 12/2013 | Barley et al. |
| 2014/0031676 A1 | 1/2014 | Nempont |
| 2014/0276937 A1 | 9/2014 | Wong et al. |
| 2015/0073400 A1* | 3/2015 | Sverdlik .......... A61B 18/082 606/28 |
| 2015/0124264 A1 | 5/2015 | Ramachandran et al. |
| 2015/0305823 A1* | 10/2015 | Claus .............. A61B 34/20 600/424 |
| 2016/0081760 A1* | 3/2016 | Verard ............. A61B 34/10 600/424 |
| 2016/0242854 A1 | 8/2016 | Grass |

* cited by examiner

ENDOGRAFT VISUALIZATION WITH OPTICAL SHAPE SENSING

CROSS-REFERENCE TO PRIOR APPLICATIONS

This application is the U.S. National Phase application under 35 U.S.C. § 371 of International Application Serial No. PCT/IB2016/050077, filed on Jan. 8, 2016, which claims the benefit of U.S. Application Ser. No. 62/106,271, filed on Jan. 22, 2015. These applications are hereby incorporated by reference herein.

BACKGROUND

Technical Field

This disclosure relates to medical instruments and more particularly to systems, devices and methods for endograft placement and deployment with shape sensing optical fibers.

Description of the Related Art

Optical shape sensing (OSS) uses light along a multicore optical fiber for device localization and navigation during surgical intervention. One principle involved makes use of distributed strain measurement in the optical fiber using characteristic Rayleigh backscatter or controlled grating patterns. The shape along the optical fiber begins at a specific point along the sensor, known as the launch point (or z=0), and the subsequent shape position and orientation are relative to that point. For meaningful clinical use, shape-sensed devices can be registered to an imaging frame of reference (such as a pre-operative computed tomography (CT) or a live fluoroscopy image).

Endovascular aneurysm repair (EVAR) has replaced open surgery as the most common technique for the repair of abdominal aortic aneurysms (AAA). The procedure is typically carried out under x-ray fluoroscopy guidance and uses significant amounts of contrast to position and deploy the stent graft correctly. On average 50-100 mL of contrast dye is used during an EVAR procedure, which may result in acute renal failure in rare cases.

The most common complication from EVAR is endoleaks resulting from an insufficient seal of the stent graft to the aorta. Endoleaks involve incorrect flow around the stent (for example, flow around the stent at the proximal or distal attachment site, flow through the graft wall, retrograde flow from the branches, etc.).

Another complication around EVAR involves ischemia of the aortic side branches (such as the colonic, renal, and pelvic arteries). This can occur due to misplacement of the stent graft such that the stent partially or completely covers one of the side vessels. This is associated with a lack of high-quality imaging technology as well as the experience of the endovascular team.

In EVAR, stent grafts are contained within a stent-deployment system that is used to navigate the endograft to the correct part of the vasculature. The deployment systems tend to be relatively large and stiff endovascular devices. They typically involve a handle or set of knobs and dials or wires at the proximal end to control the various steps around the stent deployment. The stent lies within a distal part of the device and is only released once the device has been navigated to the appropriate location. In some cases, the stent completely deploys in one step, while in other cases the stent can be partially deployed to allow for correct positioning and orientation before the final deployment step firmly attaches the stent to the vasculature (typically through a retaining/sealing ring).

The endovascular stent graft requires a sufficient amount of healthy vasculature where it can land its sealing ring. If this is not possible beneath the renal arteries, then the endograft will cover those arteries, and must create some alternative way of maintaining flow to those vessels. This can be done with a fenestrated stent (e.g., a stent with windows for the side-branches) in a procedure known as fenestrated endovascular aneurysm repair (FEVAR). In this case, the stent has fenestrations that must be lined up correctly with the side branches and additional stents are placed to connect the side vessels to the main stent.

Under x-ray guidance the endograft can be visualized through x-ray visible markers that are located in key positions on the endograft. In a fenestrated endograft, the markers identify the locations of the fenestrations and can be used to orient the stent to appropriately align the fenestrations with the side vessels. Complications from EVAR include misplacement of the endograft resulting in endoleaks, misplacement of the endograft resulting in occlusion of the side branches, contrast nephropathy due to high levels of contrast used during endograft deployment and high contrast and radiation dose due to long procedure times due to navigation and deployment in a complex anatomy. In addition, placement of a three-dimensional stent within a three-dimensional anatomy is challenging and is typically performed under two-dimensional imaging guidance through x-ray fluoroscopy.

SUMMARY

In accordance with the present principles, a system for medical device deployment includes at least one optical shape sensing (OSS) system associated with at least one of a deployable medical device and a deployment instrument. The OSS system is configured to measure at least one of shape, position or orientation of the deployable medical device and/or deployment instrument. A registration module is configured to register OSS data with imaging data to permit placement of the deployable medical device. An image processing module is configured to create a visual representation of the deployable medical device and to jointly display the deployable medical device with the imaging data.

A system for implantable device deployment includes at least one OSS system associated with at least one of an implantable device and a deployment instrument, the OSS system being configured to measure at least one of shape, position or orientation of the implantable device and/or deployment instrument. An editing module is configured to modify a digital representation of the implantable device type by modifying a model or mesh of the implantable device to fit a blood vessel. A registration module is configured to register OSS data with imaging data to permit placement of the implantable device using the digital representation. An image processing module is configured to display the digital representation of the implantable device with the imaging data.

A method for deploying a medical device includes selecting a deployable medical device model as a digital representation of a deployable medical device; registering OSS data for an OSS enabled deployment instrument with imaging data; jointly displaying the OSS data of an OSS system, the digital representation and the imaging data to provide guidance in positioning the deployable medical device using the digital representation; and deploying the deployable medical device in a blood vessel using a visual display of the digital representation of the deployable medical device.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
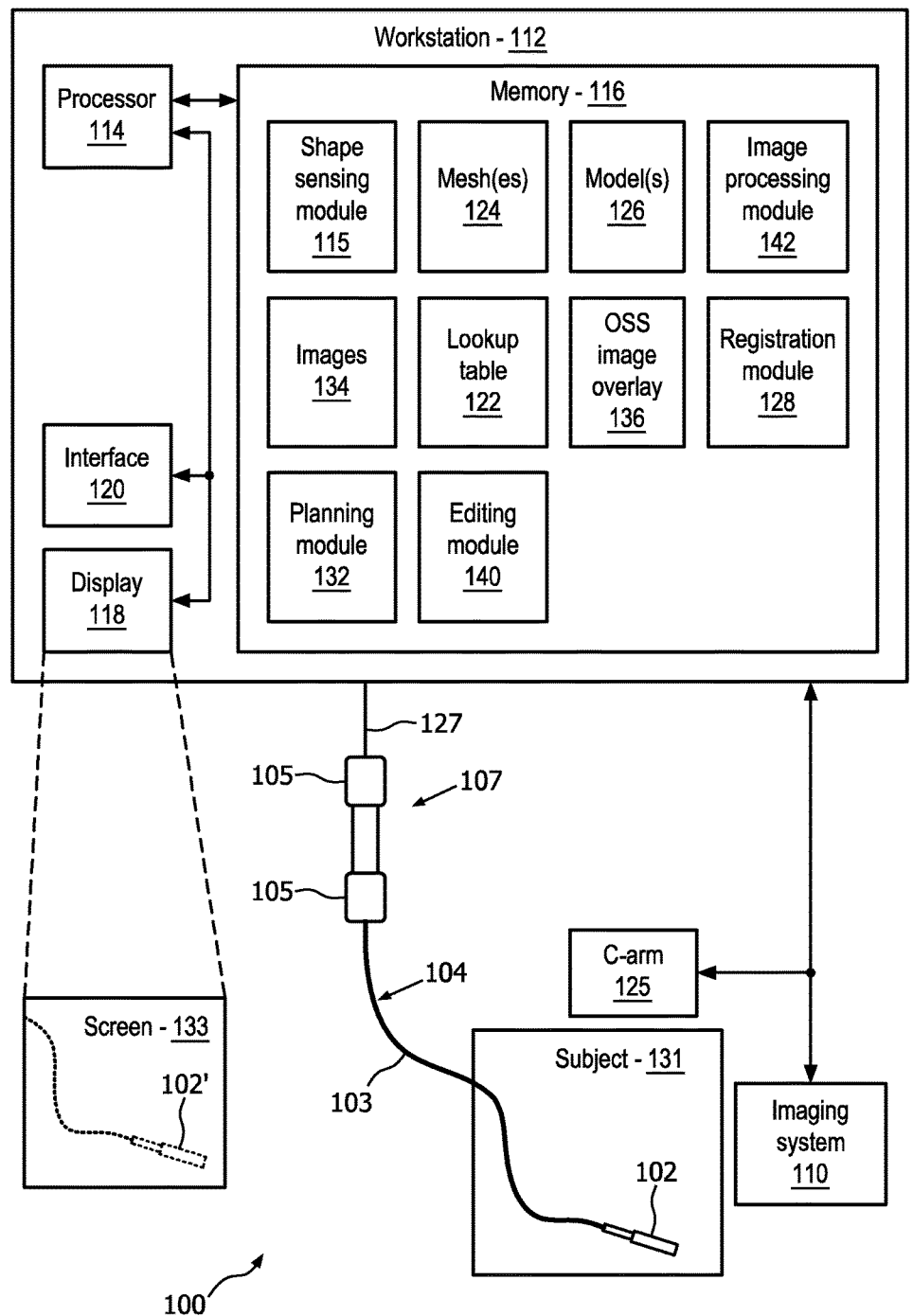
FIG. 1 is a block/flow diagram showing a system for endograft planning and deployment in accordance with one embodiment.

In accordance with the present principles, a three-dimensional visualization of an endograft with respect to anatomic imaging (e.g., a pre-operative computed tomography (CT) image, an intra-operative xperCT/3DRA, a fluoroscopy roadmap, ultrasound, etc.) can be more accurately controlled during deployment using optical shape sensing (OSS). Introducing OSS for navigation in endovascular aneurysm repair (EVAR) can reduce radiation and contrast dose and provide a more intuitive way to position catheters and guidewires within a three-dimensional vasculature to reduce procedure times and improve outcomes.

One feature of EVAR procedures is the deployment of an endograft. The orientation and position of the endograft is an important consideration in making a good seal with the vessel and adjusting the flow such that an aneurysm is no longer under pressure. If the endograft is not positioned correctly, blood may leak around the stent graft and continue to pool in an aneurysm sac, or the endograft could occlude side-vessels off the aorta which can cause poor blood flow to critical organs. In fenestrated endovascular aneurysm repair (FEVAR), side-branches (such as the renal arteries) need to be cannulated. This cannulation involves navigating a catheter and guidewire through a semi-deployed stent graft, exiting the stent graft via a fenestration, and then entering the target vessel. While this can be done largely through the known position and shape of the devices through OSS, it may also be advantageous to see the position of the endograft (and corresponding fenestrations). Thus, by shape sensing the endograft, the endograft position/orientation/shape can be tracked during deployment for optimal positioning and cannulation of side-vessels can be performed without (or with minimal) use of x-ray guidance. In one embodiment, guidance can be performed based on OSS-enabled devices, an OSS-enabled stent graft, and a pre-operative CT/live fluoroscopy.

In some cases, it may not be suitable or possible to directly shape sense the entirety of the endograft. In such cases, the information may be for a single position on the endograft, the position and orientation of the stiff guidewire, the position, orientation, and state of the deployment based on a handle of the deployment device used in conjunction with an OSS-enabled stiff guidewire or other combinations, subsets or scenarios employing OSS data. To provide the operator with knowledge of the endograft shape, position, and orientation it is possible to introduce optical shape sensing guidance to the endograft deployment process.

In accordance with the present principles, a priori models may be employed for the endograft (or stent graft), coupled with the intraoperative OSS data, as well as any live imaging of the endograft to provide a 3D representation of the endograft to the user. In addition, mechanisms for aiding in the navigation, positioning, and alignment of the endograft are described including pre-procedure planning and targeting. The present principles predict a 3D model of an interventional device (such as an endograft, balloon, etc.) with at least partial information about its state of deployment using shape sensing. That predicted model can then be updated using any additional fluoroscopy/imaging information. Three dimensional (3D) models of devices depend on each device type and brand as well as information about its state of deployment. The models and eventually the devices themselves are updated using the OSS data collected. When the endograft in positioned, its placement and deployment are more accurately provided, hence reducing exposure to imaging radiation during a procedure, ensuring a better fit and reducing complications associated with poorly fitted endografts.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for tracking and navigation of endografts and related accessories or tools with shape sensing enabled devices and systems is illustratively shown in accordance with one embodiment. The navigation may be manual, computer assisted or robotically performed. System 100 may include a workstation or console 112 from which a procedure is supervised and/or managed. Workstation 112 preferably includes one or more processors 114 and memory 116 for storing programs and applications. Memory 116 may store an optical sensing module 115 configured to interpret optical feedback signals from one or more shape sensing devices or systems 104. Optical sensing module 115 is configured to use the optical signal feedback (and any other feedback, e.g., electromagnetic (EM) tracking, x-ray or ultrasound images) to reconstruct deformations, deflections and other changes associated with a deployable medical device or instrument 102, such as an endograft, stent, balloon, etc. Device 102 may also include a guidewire, catheter or other medical device.

A shape sensing system 104 includes one or more optical fibers 127 which are included in the system 104 in a set pattern or patterns. The optical fibers 127 connect to the workstation 112. The shape sensing system 104 may be included in one or more devices, such as in a deployment system 107, a handle 105 (for the deployment system 107 or for a guidewire or catheter), a catheter or guidewire 103, a deployable device 102 (also referred to herein as endograft 102) or other medical component, etc. The OSS fibers 127 or OSS systems 104 are employed to create a visual representation of an endograft, stent, or markers, or through the use of pre-procedure planning used in combination with optical shape sensing for endograft or other device deployment. The present principles apply to any use of an optical shape sensing fiber 127 for navigation and deployment of device 102, or deployment system 107. The present principles can also apply to balloon catheters, clips, valves, and other implantables, e.g., occlusion devices, stents, drug eluting stents, drug coated balloons, lung volume reduction devices, etc.

In one embodiment, the fibers 127 of the OSS system 104 are integrated within the endograft 102. In other embodiments, the OSS fibers may be integrated into the deployment system 107 (which may also include a handle(s) 105) or the guidewire 103 (e.g., a stiff guidewire). An OSS system 104 can be employed for making physical measurements for planning or for placement of an endograft 102 or stent. In one embodiment, the endograft 102 or stent may include an OSS system 104 to provide position and orientation information for the endograft 102 or stent.

Shape sensing system 104 with fiber optics may be based on fiber optic Bragg grating sensors in one or more optical fibers. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, strain causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

It should be understood that optical shape sensing may be performed in a plurality of ways and is not limited to FBGs or Rayleigh scatter techniques. For example, other techniques may include channels etched into the fiber, employing quantum dots for reflection, employing a plurality of separate fibers (e.g., 3 or more) instead of a single multicore fiber or other optical shape sensing techniques.

A 3D representation 102' (e.g., a mesh 124 or model 126) of the endograft 102 can be created and positioned in a displayed image using OSS measurements. In one embodiment, for each endograft type, a series of images 134 (e.g., CT) are acquired a priori for a deployment of the endograft 102. This is employed to build a lookup table 122 between a model type, deployment state, and a mesh representation of the endograft 102 or, a representative model of the stent is created as a numerical mesh. In other words, the lookup table 122 includes different models for a visualized object (on a display) in various deployment states, which is then oriented to match the orientation detected by OSS data. Using optical shape sensing data from the endograft (or deployment system 107, stiff guidewire 103, etc.), the visual representation 102' of the device 102 (endograft) is created. The visual representation 102' can be made from an a priori model 126 of a given endograft type, or it can be made from a standard model. The visual representation 102' is then positioned and oriented relative to intraoperative (or preoperative) images 134 according to the OSS measurement of the device 102. This representation 102' can also be updated using information from the intraoperative imaging, user input, information from the deployment device as to the state of the deployment, etc.

Pre-operative planning can be done using the representation 102' and can be used to help the operator as they position the actual endograft using OSS guidance. In addition, an OSS-enabled catheter or guidewire (103) can be used ahead of time to size some of the vessel positions and lengths to help the operator as they select and then position the representation 102'.

During a procedure, the known information about the endograft 102 is employed to look up a closest a priori endograft mesh 124 or model 126. The input information may include, e.g., the endograft type (manufacturer, model number, etc.), the state of deployment (partially deployed, fully deployed, deployment configurations, etc.) and/or user input. Input information may also include an OSS fiber (or alternative sensing mechanism) to know the position of relevant features on the handle 105 of deployment device (103), the known OSS positions of attachment point(s) on the endograft 102, the known OSS position of a sheath or other components of the deployment system 107.

If instead of an a priori endograft mesh 124, the representative model 126 may be used, then it can be inflated/deformed to the appropriate state based on knowledge of the state of the deployment (as described above).

The endograft mesh 124 is transformed to the correct position and orientation based on shape sensing knowledge of the position and orientation of the stiff guidewire 103, handle 105, deployment device 107, or specific point(s) on a stent or endograft 102. The endograft mesh 124 may be deformed to the correct shape based on the shape of the stiff guidewire 103, the known OSS position of attachment point(s) on the endograft 102, the shape of the deployment device 107 (from an OSS fiber embedded in the device), the known state of deployment (based on the known position of a sheath housing the endograft, for example), etc. This will give the endograft 102 any necessary curves relevant to the specific patient anatomy.

In the event that the operator uses a fluoroscopy image (e.g., image 134) to confirm the position of the stent graft 102, the model of the stent graft 102 can be updated using marker positions detected from the fluoroscopy image (134). These markers can be automatically or semi-automatically identified, or selected in the image 134 by the operator. Alternatively, the user may have the ability to manually adjust the model using a graphical user interface (120) on a display 118.

Sizing of a main body endograft 102 and limb extensions, etc. is of primary importance in making sure that no branching vessels are occluded. For example, if a limb extension into the main iliac is too long then it can block the internal iliac. An OSS system 104 can be employed to confirm the selection of these endografts. Once the OSS-enabled device or system 104 has been navigated into the aorta, positions or targets can be identified on the fluoroscopy image (134) and OSS overlay image 136. The length of OSS fiber (127) can then be used to determine the length of vessel between those positions. This can eliminate miscalculations of these lengths due to foreshortening, which is a known issue with fluoroscopy-based measurements.

Workstation 112 includes a display 118 for viewing internal images of a subject (patient) or volume 131 and may include the image 134 or the image 136 as an overlay or other rendering registered with the shape sensing system 104 in one or more of the components employed in the procedure. Display 118 may also permit a user to interact with the workstation 112 and its components and functions (e.g., touchscreen, graphical user interface, etc.), or any other element within the system 100. This is further facilitated by an interface 120 which may include a keyboard, mouse, a joystick, a haptic device, or any other peripheral or control to permit user feedback from and interaction with the workstation 112.

A registration module 128 is configured to register the OSS fiber 127 or system 104 to a physical structure (e.g., aneurysm, etc.), OSS systems 104, images 134, 136, etc., endograft 102 to OSS systems, etc. For shape recognition registration, a distinctive shape can be employed to obtain both position and orientation information from the fiber 127. If the fiber 127 takes a predefined and immutable path, the curvature and shape information of that path can be used to identify a unique image to fiber transformation to be stored in memory 116.

An image processing module 142 is configured to combine images (134) and OSS position data (image 136) for joint or separate display on the display 118. OSS data (from, for example, image 136 or position and shape information derived from the fiber 127 or curvature and shape information of the fiber 127) and the image data (from pre-operative or intraoperative images 134) can be registered and jointly displayed on a display screen 133 to assist in placement of the endograft 102 (or other stent or implantable device) by employing the representation 102' (e.g., a rendered version of the model 126) of the endograft 102. The representation 102' is registered to the OSS data and rendered in the display on screen 133 to enable a user to visualize the endograft 102 during its placement and deployment.

OSS measurement is also particularly useful in measuring anatomical structures for determining an endograft or stent to be placed. In addition, the OSS system(s) 104 may be employed to evaluate endograft stress and flow modeling. Once an endograft 102 is deployed the position of an endograft sealing ring, main body, and other components (see, e.g., FIGS. 5 and 6) can have a significant effect on the stresses experienced by portions of the endograft 102. If there is excessive stress on a part of the graft 102, the stress can lead to endograft failure, migration, and ultimately necessitate a re-intervention. In addition, if the graft 102 is not placed optimally the flow through the graft can be sub-optimal. This is currently studied through a post-operative CT, at which point it is too late to change anything in the endograft placement. While post-operative CT, fluoroscopy or contrast injection to determine how the graft has shifted after implantation and healing would still be employed, confidently positioning the endograft using OSS or other means reduces the chances of the ill-effects due to poor endograft placement.

With intraoperative predictions of these effects based on the optical shape sensing information about the endograft position and orientation, the clinician can adjust the endograft 102 prior to final deployment. In useful embodiments, the shapes of the OSS system 104 can be employed to estimate flow and/or stress in the graft 102. The modeling of these flows or forces is particularly relevant to endografts that target angulated necks and that take on more tortuosity.

Figure 2:
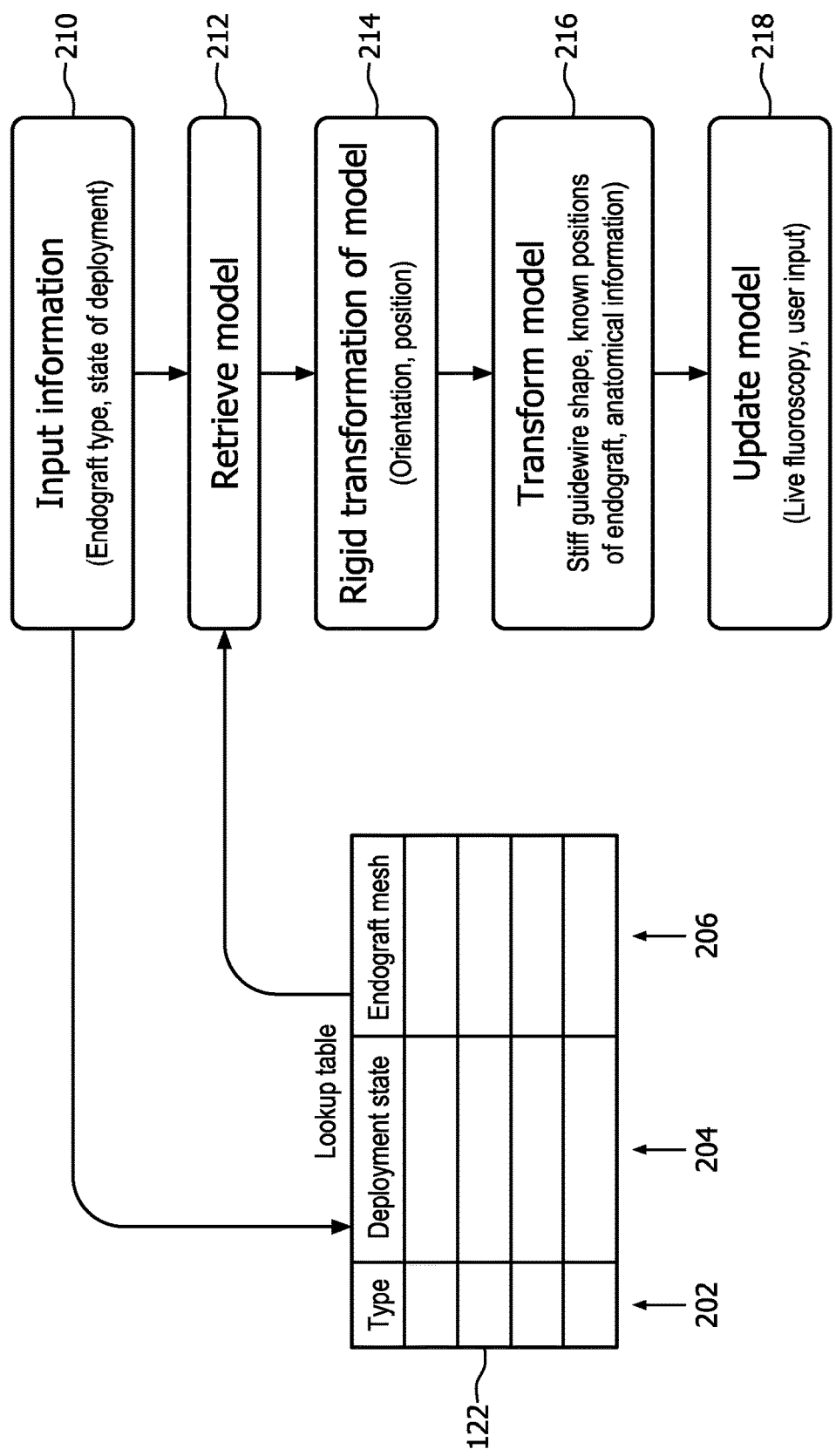
FIG. 2 is a block/flow diagram showing a method for model/mesh modification in accordance with one embodiment.

Referring to FIG. 2, an illustrative lookup table 122 is depicted in accordance with one embodiment. The lookup table 122 includes a column 202 for an endograft type, a column 204 for a state of deployment and a column 206 for an endograft mesh or model (a name, a file name, a pointing address, etc.). During a procedure, an operator may enter the endograft type and the state of deployment as input data into the workstation 112 in block 210. The endograft type and the state of deployment may also be detected automatically. The processor 114 searches the lookup table 122 (columns 202 and 204) to determine the mesh or model for the input data and retrieve the mesh or model type in block 212. In block 214, a rigid transformation of the model is performed based on the input information from the optical shape sensing fiber. In block 216, the model is transformed to conform to the anatomical information, guidewire or other deployment tool shape(s), known positions of the endograft, etc. In block 218, the stent model is updated further using live images (e.g., fluoroscopy), user input, etc. In this way, a model may be selected and modified to better represent the endograft is a visual display.

Figure 3:
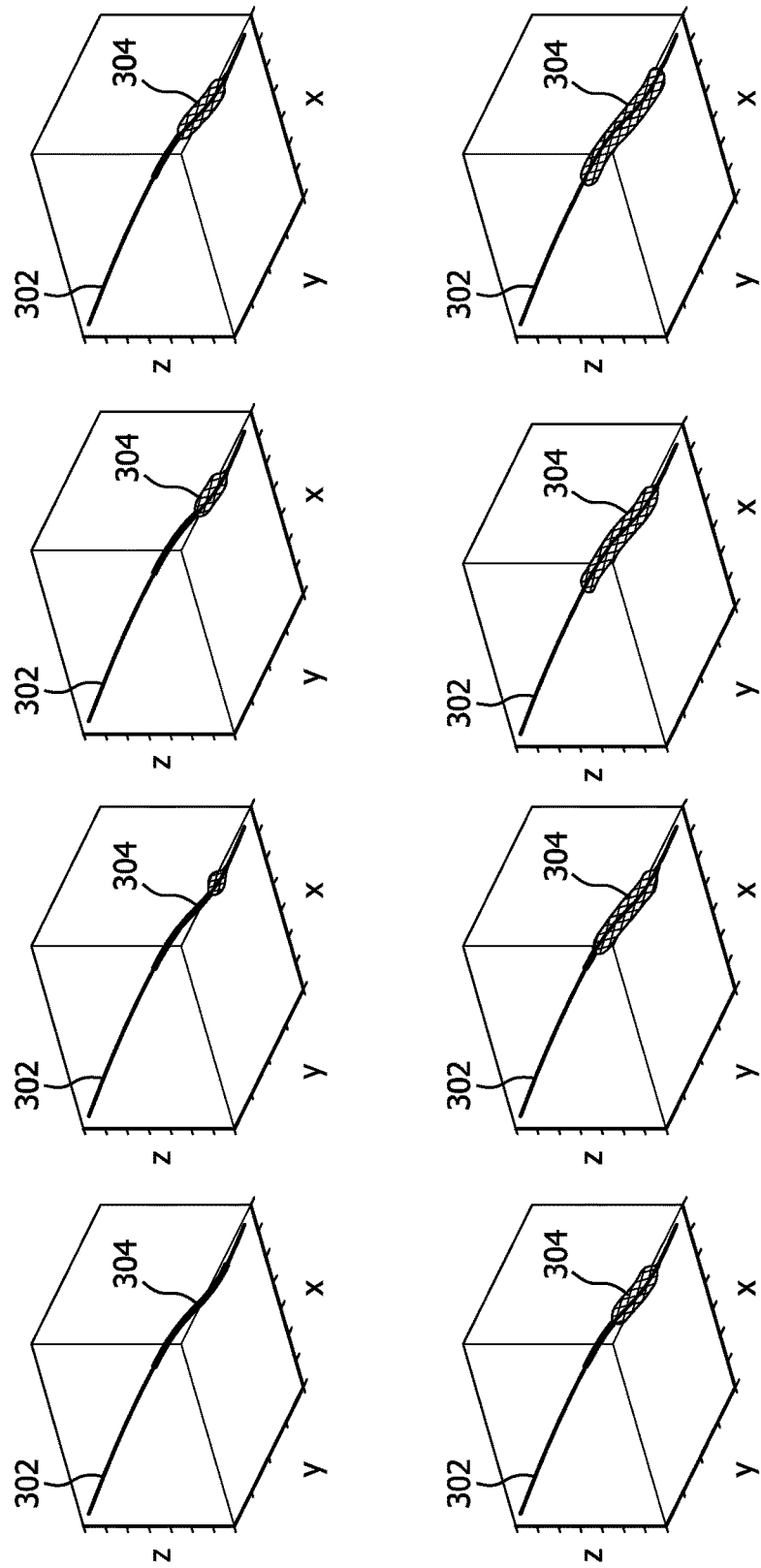
FIG. 3 shows images for deployment of a virtual endograft located in accordance with an OSS fiber in accordance with the present principles.

Referring to FIG. 3, an optical shape sensing fiber 302 is shown with a model 304 of an endograft during various stages of deployment. This model 304 can provide an easier way for clinicians to understand the position, orientation, and shape of the endograft. The cylindrical endograft model 304 can be deformed and registered to the optical shape sensing fiber 302 and displayed to allow the user to visualize the position, orientation, and state of deployment of the stent with respect to the surrounding anatomy. The image of the model 304 may be rendered along with the OSS fiber 302 to make measurements or comparisons prior to deployment of an endograft. The model 304 may include a modified model that has been updated in accordance with previous OSS measurements or other information.

Figure 4:
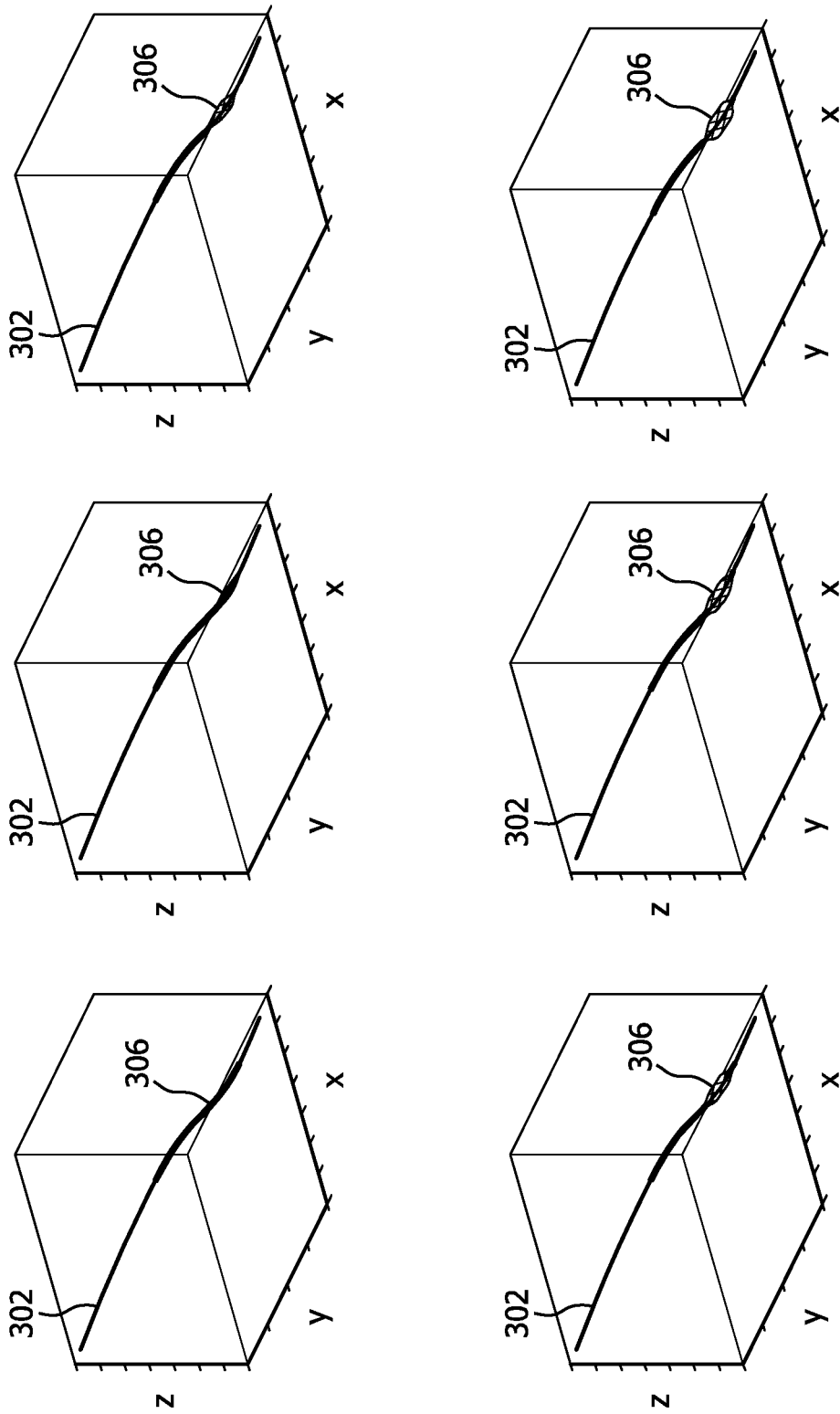
FIG. 4 shows images for deployment of a virtual balloon for endograft deployment located in accordance with an OSS fiber in accordance with the present principles.

Referring to FIG. 4, the optical shape sensing fiber 302 is shown with a cylindrical balloon catheter model 306 during various stages of deployment. This model 306 can provide an easier way for clinicians to understand the position, orientation, and shape of the balloon catheter 306. The balloon catheter model 306 can be deformed and registered to the optical shape sensing fiber 302 and displayed to allow the user to visualize the position, orientation, and state of inflation of the balloon.

Referring again to FIG. 1, the workstation 112 may include a planning module 132 that is configured to support planning a procedure for deployment of a graft or stent. The planning module 132 may employ anatomical features as measured by OSS or other methods or may use a 'standard' stent which could be selected from pre-operative images.

In accordance with the present principles, an endograft pre-procedure plan may be carried out as follows. Prior to the procedure, planning can be performed using the same lookup table 122 with the a priori endograft models or simulated endograft models 126 or meshes 124. This can be performed by loading the a priori mesh 124 of the endograft and overlaying the mesh 124 on a pre-operative CT or similar image 134. The user is permitted to adjust the shape of the endograft model 126 or mesh 124 to match the anatomy using an editing module 140 configured to modify a digital representation (124, 126) of the endograft by modifying the endograft model 126 or mesh 124 by resizing the endograft and positioning cannulation of side-vessels. This can be performed in a plurality of ways or combinations thereof. For example, one way includes manual deformation of the endograft model 126 or mesh 124 by the user (through a GUI on the display 118). Another way may include a semi-automatic deformation where the user positions a retaining ring (or some other feature(s) of the mesh 124) and then the rest of the mesh 124 deforms to match the anatomy. Yet another way may be based upon the position of other endografts deployed prior to the given endograft, e.g., an iliac limb with respect to a main body graft may be employed as a model. This could be done automatically based on the known landing zones for the marker bands and then adjusted by the user.

Once the endograft(s) have been positioned as desired, features can be extracted from the a priori model 126 and displayed or drawn or placed by the user, such as 1) Landing zone for the neck of the stent or secondary stents, 2) Targeting rings for the neck of the stent or secondary stents, 3) Target spheres or rings or set of markers for the position of the fenestrations or position of contralateral gate, which allows the user to choose to visualize only these features and hide the entire model 126, 4) Expected force profile for mechanical forces on the stent as well as a simulated flow profile through the endograft, etc.

The steps described for pre-procedure planning can also be offered intra-operatively to permit operators to predict how a graft may be positioned post deployment. The planning itself can be done on the fly, or the pre-procedure plan can be updated on the fly. This is important as the anatomy can shift significantly with the introduction of the relatively stiff deployment device into the vessels. For this same reason, fluoroscopy images taken periodically during deployment may be preferable to using a pre-operative CT image 134 for this type of navigation and deployment.

The tasks described here can also be offered to the user prior to the procedure as a simulator to prepare the operator to the specific procedure and/or to be used for general training purpose. However, to reduce this effect, the pre-operative CT image 134 can be updated based on fluoroscopy images during the procedure. For example, two angiogram images at different projections can be used to identify, for example, the renal bifurcation. If the user already has a targeting ring or sphere at that location, then the target can be adjusted based on the live angiogram images. This can similarly be done for other relevant anatomical features (iliac bifurcation, SMA, celiac, etc.). Based on how these features are adjusted, the pre-operative CT image 134 can similarly be deformed to match.

In one embodiment, to assist in visualization of the graft in an intra-operative image, a representation of the stent graft can be shown to the operator as or with a probability map or probability indicator as to the most likely position of the stent graft. The probability map may be rendered on a display indicating positions where the optimal placement or degrees of optimal placement would occur, this may be based on computations, history data (from other procedures), a zone set forth by clinicians, etc. The probability map may include different colors or textures to indicate safe placement zones or indicate areas where placement would be less desirable. The probability map may include an indicator of potential inaccuracies/uncertainties of the shape sensing data or the quality of registration, e.g., the endograft model in the display may change color, and/or the virtual vessel to indicate a better chance of success for the placement of the endograft. Different variations and use of the probability map would be understood by those skilled in the art.

Alternatively, the operator can be shown the position of markers indicating the key features of the stent graft (as opposed to the entire graft). The markers can be shown as a 3D representation, or can be projected into a 2D plane and overlaid upon a fluoroscopy image. These features may include ends, rings or other distinctive shapes to be employed to align or other position the stent graft. If the operator is using a pre-operative plan, the visualization can indicate when the current positioning of the endograft matches the plan within a certain tolerance.

In other embodiments, during the procedure, the OSS information about the endograft position can be used to limit a radiation dose to the patient (and clinicians) by limiting the radiation beam to a known region of interest around the endograft 102. This can be done by automatic or user-determined positioning of image wedges on a source of an imaging system 110. The imaging system 110 may include a fluoroscopy system, ultrasound system, etc. In one embodiment, the imaging system 110 may include a c-arm 125. The position and the angle of the c-arm 125 can be optimized by either automatically controlling its position or suggesting optimal positions to the user based on the OSS knowledge of the endograft position and orientation.

Figure 5:
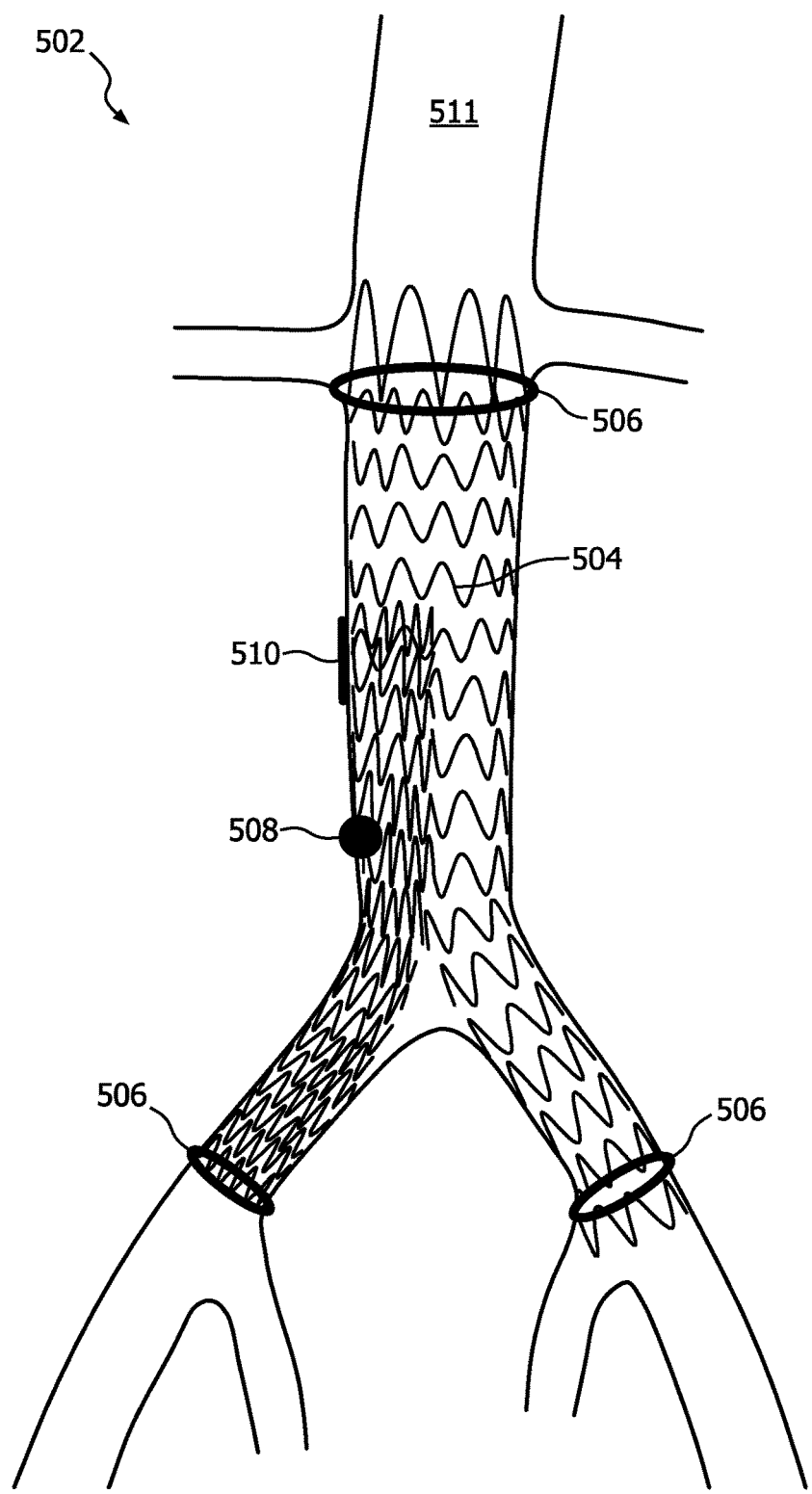
FIG. 5 is an image showing location markers for an endograft in accordance with the present principles.

Referring to FIG. 5, an example image 502 is shown for pre-procedure planning of an endograft 504 placement including targeting rings 506, spheres 508, and landing regions 510 that can be drawn during the planning stage within a blood vessel 511. These planning features can then be used during the deployment.

Figure 6:
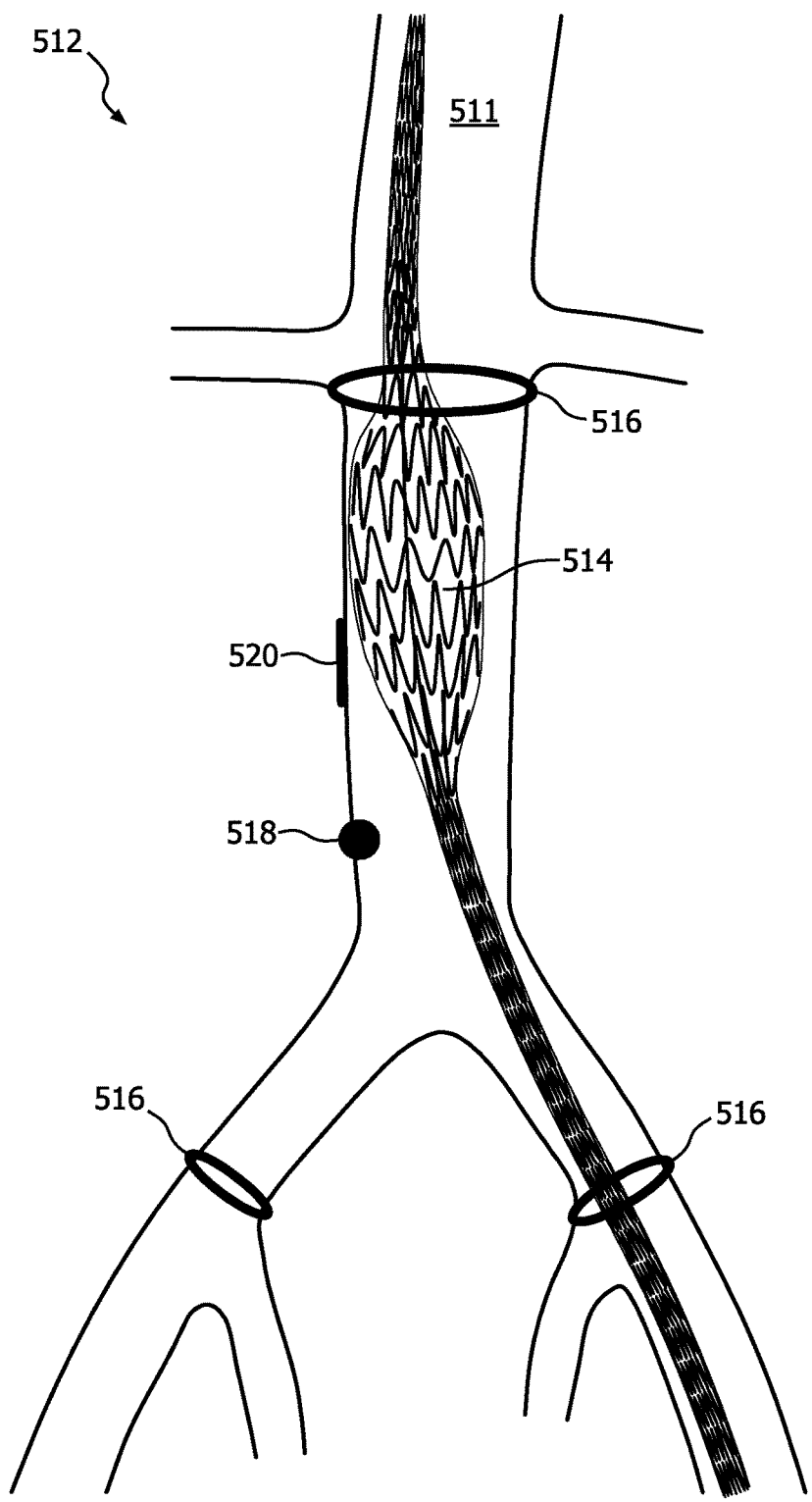
FIG. 6 is an image showing location markers for an endograft deployment in accordance with the present principles.

Referring to FIG. 6, an example image 512 is shown for pre-procedure planning of a deployment of an endograft 514 including targeting rings 516, spheres 518, and landing regions 520 that can be drawn during the planning stage. These planning features can then be used during the deployment.

It should be understood that the present principles covers any of the applications where an endograft is deployed under fluoroscopic or other imaging guidance including, but not limited to procedures, such as, e.g., endovascular aneurysm repair (EVAR), branch-fenestrated EVAR (BEVAR), percutaneous EVAR (PEVAR), thoracic EVAR (TEVAR), fenestrated EVAR (FEVAR), etc.

Figure 7:
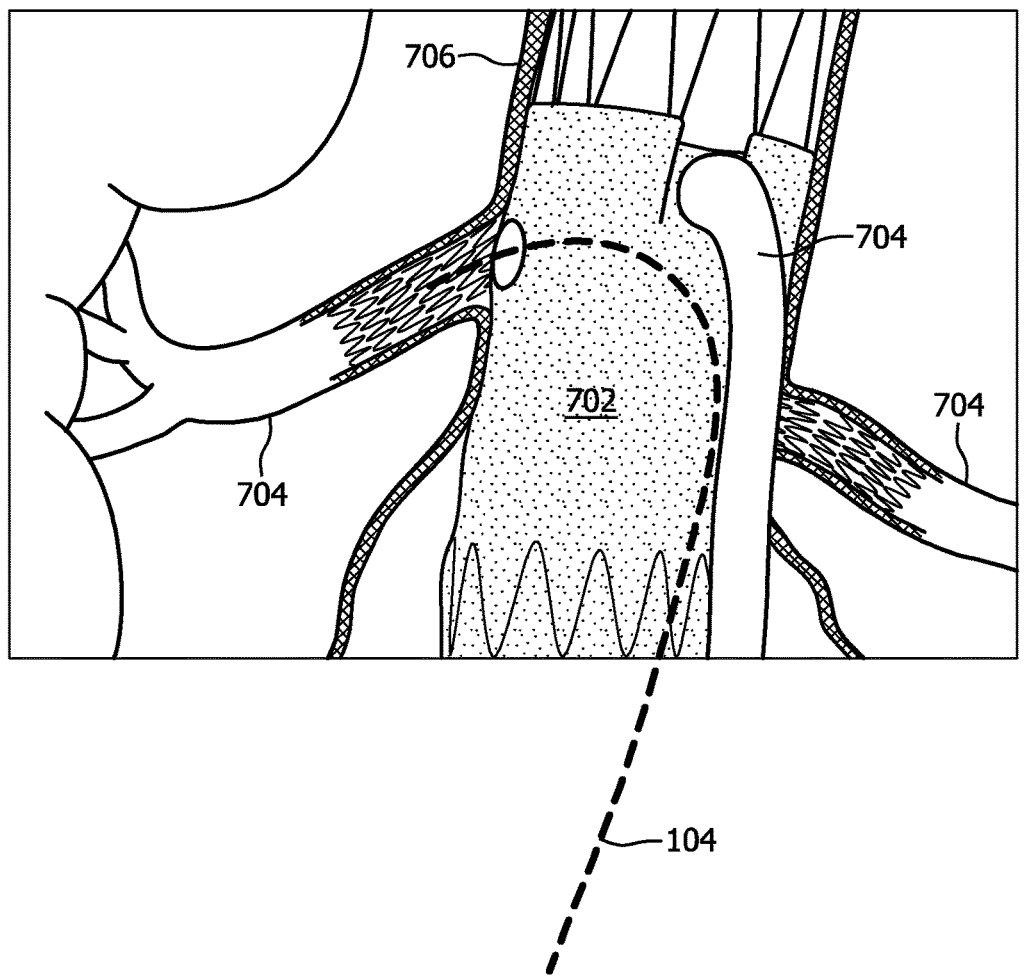
FIG. 7 is an image showing placement and cannulation of an endograft in accordance with the present principles.

Referring to FIG. 7, a fenestrated stent graft (endograft) 702 is shown for an endovascular aneurysm repair (EVAR) procedure in accordance with the present principles. A position and orientation of the graft 702 was planned using an OSS system 104 prior to its placement. In addition, the locations and sized of branches 704 of a blood vessel 706 were determined. The present principles use a priori models of a stent graft, coupled with intraoperative OSS data, as well as any live imaging of the stent graft, to compensate for lack of information and provide a 3D representation of the stent graft to the user.

The model of the endograft 702 is modified using an editing tool (editing module 140, FIG. 1) followed by the manufacture of the graft 702 in accordance with the modifications. The modifications may include branch positions, sizes of the endograft 702 (lengths and diameters at particular positions, etc.). This ensures that the endograft 702 will fit well once deployed. The graft 702 is then deployed. The endograft 702 may include an OSS system 104 integrated therein, which may include an OSS fiber, an OSS enabled catheter, an OSS enabled guidewire, etc. The OSS system 104 and intraoperative imaging are jointly employed to locate a position, shape and orientation of the graft relative to the blood vessel 706.

The branches 704 are aligned with corresponding structures on the endograft 702 and the rings or ends of the endograft 702 are placed on healthy tissue adjacent to an aneurysm or other damaged tissue. The endograft may be deployed with or on a deployment tool or instrument (e.g., a guidewire, a catheter (e.g., a balloon catheter) or any other instrument). The deployment tool (107, FIG. 1) may include an OSS system 104 instead of or in addition to the one in the endograft 702. The deployment tool 107 (FIG. 1) with an OSS system 104 may assist in ensuring accurate placement of the graft 702. The orientation and position of the endograft 702 is important to making a good seal with the blood vessel 706 and adjusting the flow such that the aneurysm is no longer under pressure. If the endograft 702 is not positioned correctly, blood may leak around the stent graft 702 and continue to pool in the aneurysm sac, or the endograft 702 could occlude side-vessels off the blood vessel 706 (e.g., aorta) which can cause poor blood flow to critical organs.

In fenestrated endovascular aneurysm repair (FEVAR), cannulating the side-branches (such as the renal arteries) may be performed in advance by mapping out the blood vessel 706 in advance of deployment of the graft 702. This cannulation involves navigating a catheter and guidewire through a semi-deployed stent graft, exiting the stent graft 702 via a fenestration, and then entering a target vessel (branch 704).

The OSS system(s) 104 track the position, orientation and shape of the endograft 702 during deployment for optimal positioning. Cannulation of side-vessels may be performed without (or with minimal) use of x-ray guidance and can be done based OSS system(s) 104 devices (e.g., one or more of an OSS enabled deployment tool, an OSS-enabled stent graft, and/or a pre-operative CT or live fluoroscopy).

Figure 8:
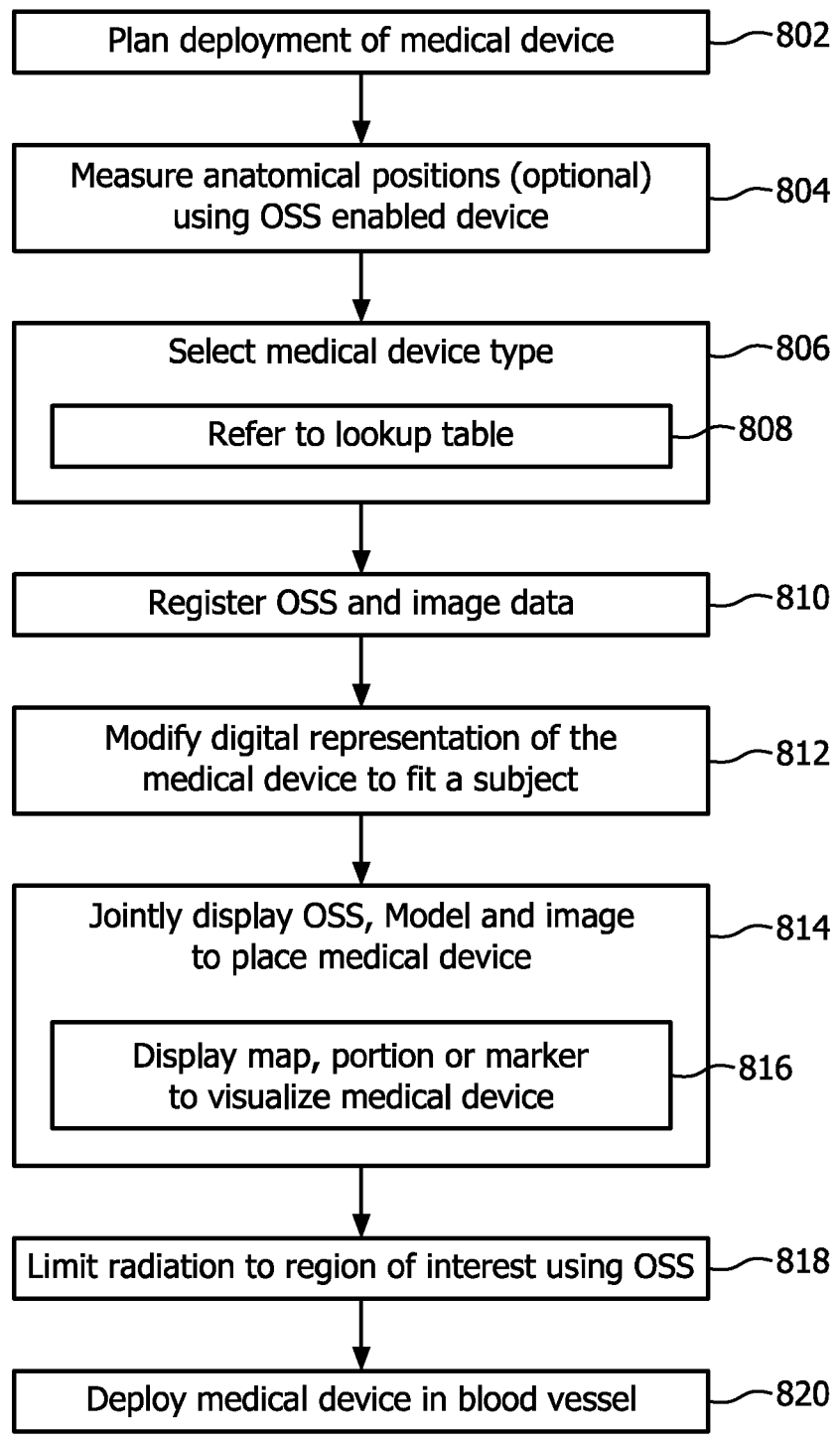
FIG. 8 is a flow diagram showing a method for planning and deployment of an endograft in accordance with an illustrative embodiment.

Referring to FIG. 8, a method for medical device deployment is described and shown in accordance with illustrative embodiments. In block 802, pre-operative planning may be conducted based on a preoperative images and a model of a deployable medical device or implantable device. The deployable medical device or implantable may include an endograft, a stent, a balloon, a clip, valve, other implantable devices, other deployable devices (e.g., catheter, guidewire, etc.). In block 804, anatomical positions (e.g., branches, landing zones, etc.) are optionally measured using an OSS-enabled device such as a guidewire or catheter. This step may include using the OSS system to make length measurements of relevant geometric features (e.g., branch locations, overall length, etc.). In certain circumstances block 804 may be skipped, e.g., the clinician could move straight from block 802 to block 806 without making measurements provided by OSS.

In block 806, an endograft type is selected. This may be based upon the measurements measured by the OSS system in block 804. In block 808, selecting an endograft type may include referring to a lookup table stored in memory and configured to index the measurements against endograft type such that a best fit endograft type is selected based upon the measurements obtained using by the OSS system. A digital representation of the endograft type is provided for the selected type.

In block 810, an OSS device for determining a position of the medical device (e.g., endograft) is registered with images of a blood vessel where the device is to be placed. OSS data is preferably registered with image data for the blood vessel. The OSS device may be integrated into a deployment system during manufacturing, may be clipped onto a handle of a deployment system, may be connected to the endograft, etc.

In block 812, the digital representation of the medical device may be modified based on inputs (e.g., position and orientation of the deployable medical device from the OSS data, state of deployment, input from the imaging data and/or user input). This may include modifying an endograft model or mesh and pre-positioning features for side-vessels to fit a subject. The OSS system may be integrated within the deployment instrument or system and at least a portion of the endograft may be virtually represented relative to the deployment instrument. By customizing the endograft in advance of deployment, the amount of time needed for fenestration and placement is greatly reduced. In addition the amount of radiation time and contrast dye(s) may also be reduced due to the use of the OSS system(s).

In block 814, OSS devices, medical device representations, and images (CT, x-ray) are jointly displayed. The OSS data and the image data are jointly displayed to permit accurate placement of, e.g., the endograft in the blood vessel. The OSS system may be integrated within the endograft, and the endograft may be visually represented by at least a portion of the endograft in the jointly displayed image. In block 816, the at least a portion of the endograft may include a probability map, a portion of the endograft or markers.

In block 818, imaging energy is limited based on region of interest focus using OSS information of endograft position and orientation. For example, the radiation may be limited to a region of interest designated by a position of a deployed OSS system. In this way, an OSS position is employed to target the radiation and the radiation may be reduced to that region/area of interest. Energy form ultrasound or other imaging modality may also be limited in the same manner.

In block 820, the endograft is deployed in a blood vessel, e.g., by expanding a balloon catheter, etc. Correction and checks may be performed on the placement or the endograft before affixing the endograft in place.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for endograft visualization with optical shape sensing (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for deployment of a medical device in an anatomical structure of a subject, the system comprising:
   an optical shape sensing (OSS) system associated with at least one of a deployable medical device or a deployment instrument for placing the deployable medical device in the anatomical structure, the OSS system being configured to measure at least one of shape, position or orientation of the deployable medical device and/or the deployment instrument, to measure at least one feature of the anatomical structure, and to provide OSS data indicating the measured at least one of the shape, position or orientation of the deployable medical device and/or the deployment instrument and the measured at least one feature of the anatomical structure;
   a processor; and
   a memory for storing instructions and a lookup table,
   wherein the lookup table stores a plurality of types of deployable medical devices, a plurality of deployment states of the types of deployable medical devices, and a plurality of previously derived models or meshes corresponding to the plurality of deployment states of the types of deployable medical devices,
   wherein, when executed by the processor, the instructions cause the processor to:
      register the OSS data with imaging data to permit placement of the deployable medical device;
      determine a type of the deployable medical device and a state of deployment of the deployable medical device;
      determine a model or mesh of the deployable medical device from the plurality of previously derived models or meshes in the lookup table based on the determined type and state of deployment of the deployable medical device;
      create a visual representation of the deployable medical device using the model or mesh of the deployable medical device; and
      jointly display the visual representation of the deployable medical device with the imaging data, wherein the visual representation is positioned according to the OSS data.

2. The system as recited in claim 1, wherein the determined model or mesh is updated in accordance with one or more of the measured at least one of the shape, position or orientation of the deployable medical device from the OSS data, the state of deployment of the deployable medical device, and input from the imaging data and/or user input.

3. The system as recited in claim 1, wherein the plurality of previously derived models or meshes stored in the lookup table comprise one or more digital representations of the deployable medical device.

4. The system as recited in claim 1, wherein the imaging data includes an intra-operative imaging system having a source that provides energy limited to a region of interest designated by a position of the OSS system.

5. The system as recited in claim 1, wherein the OSS system is integrated within the deployable medical device.

6. The system as recited in claim 5, wherein at least a portion of the deployable medical device is visually represented on a display using a probability map, a portion of the deployable medical device or markers.

7. The system as recited in claim 1, wherein the OSS system is integrated within the deployment instrument and at least a portion of the deployable medical device is virtually represented relative to the deployment instrument.

8. The system as recited in claim 1, wherein the deployable medical device includes one or more of: an endograft, a stent, a replacement valve, a clip or a balloon.

9. The system as recited in claim 1, wherein the stored instructions further cause the processor to modify the determined model or mesh based on at least one of the OSS data or the imaging data of the deployable medical device.

10. The system as recited in claim 1, wherein the deployable medical device comprises a balloon, and wherein the state of deployment of the deployable medical device includes an amount of inflation and/or deformation of the balloon.

11. A system for deployment of an implantable device in an anatomical structure of a subject, the system comprising:
an optical shape sensing (OSS) system associated with at least one of the implantable device or a deployment instrument, the OSS system being configured to measure at least one of shape, position or orientation of the implantable device and/or the deployment instrument, and to measure at least one feature of the anatomical structure; and
a processor; and
a memory for storing instructions and a lookup table,
wherein the lookup table stores a plurality of types of deployable medical devices, a plurality of deployment states of the types of deployable medical devices, and a plurality of previously derived models or meshes corresponding to the plurality of deployment states of the types of deployable medical devices, and
wherein, when executed by the processor, the instructions cause the processor to:
determine a type of the implantable device and a state of deployment of the implantable device;
determine a model or mesh of the implantable device from the plurality of previously derived models or meshes in the lookup table corresponding to the determined type and state of deployment of the implantable device;
modify a digital representation of the determined type of the implantable device by modifying the model or mesh of the implantable device to fit a blood vessel;
register OSS data with imaging data to permit placement of the implantable device using the digital representation; and
display the digital representation of the implantable device with the imaging data, wherein the digital representation is positioned according to the OSS data.

12. The system as recited in claim 11, wherein the digital representation of the determined type of the implantable device is modified in accordance with at least one of shape, position and orientation of the implantable device from the OSS data, a state of deployment of the implantable device, input from the imaging data or user input.

13. The system as recited in claim 11, wherein the imaging data includes an intra-operative imaging system having a source that provides energy limited to a region of interest designated by a position of a deployed OSS system.

14. A method for deploying a deployable medical device in an anatomical structure of a subject, the method comprising:
measuring at least one feature of the anatomical structure using optical shape sensing (OSS);
selecting a type of the deployable medical device based upon the measured at least one feature of the anatomical structure;
accessing a lookup table that stores a plurality of types of deployable medical devices, a plurality of deployment states of the types of deployable medical devices, and a plurality of deployable medical device models corresponding to the plurality of deployment states of the types of deployable medical devices;
determining a deployable medical device model from the plurality of deployable medical device models from the lookup table, based on at least the selected type of the deployable medical device and a state of deployment of the deployable medical device, as a digital representation of the deployable medical device;
registering OSS data for an OSS enabled deployment instrument with imaging data;
jointly displaying the digital representation of the deployable medical device positioned according to the OSS data and the imaging data to provide guidance in positioning the deployable medical device; and
deploying the deployable medical device in a blood vessel using a visual display of the digital representation of the deployable medical device.

15. The method as recited in claim 14, further comprising:
updating the digital representation of the deployable medical device in accordance with at least one of measured shape, position or orientation of the deployable medical device from the OSS data, and the state of deployment of the deployable medical device.

16. The method as recited in claim 14, wherein the imaging data includes intra-operative imaging data from a source that provides energy limited to a region of interest designated by the OSS data.

17. The method as recited in claim 14, wherein at least a portion of the digital representation of the deployable medical device is displayed using a probability map.

* * * * *